United States Patent [19]

Ona et al.

[11] Patent Number: 4,614,675

[45] Date of Patent: Sep. 30, 1986

[54] ANTIMICROBIC, ANTISTATIC SILOXANE COMPOSITIONS AND METHOD FOR TREATING MATERIALS

[75] Inventors: Isao Ona; Masaru Ozaki, both of Chiba, Japan

[73] Assignee: Toray Silicone Co., Ltd., Tokyo, Japan

[21] Appl. No.: 811,576

[22] Filed: Dec. 20, 1985

[30] Foreign Application Priority Data

Dec. 21, 1984 [JP] Japan .................................. 59-271346

[51] Int. Cl.$^4$ .............................................. B05D 3/02
[52] U.S. Cl. .................................... 427/387; 428/447; 523/122; 524/730; 524/731; 524/910; 524/911; 524/912; 524/913; 424/78; 528/33; 528/34; 528/35; 528/38
[58] Field of Search ........................ 427/387; 428/447; 523/122; 524/730, 731, 910, 911, 912, 913; 424/78; 528/33, 34, 35, 38

[56] References Cited

U.S. PATENT DOCUMENTS

| | | | |
|---|---|---|---|
| 4,500,337 | 2/1985 | Young et al. | 424/78 |
| 4,500,338 | 2/1985 | Young et al. | 424/78 |
| 4,500,339 | 2/1985 | Young et al. | 424/78 |

*Primary Examiner*—Melvyn I. Marquis
*Attorney, Agent, or Firm*—George A. Grindahl

[57] ABSTRACT

A composition for treating a solid material to give it antimicrobic, hydrophilic and antistatic properties comprises siloxane compound which has one or more alkoxysilylalkyl groups and one or more polyoxyalkylene groups and a silane having antimicrobial properties. In a preferred embodiment the composition is used to treat fibers and fiber-containing materials. The composition can further contain a curing agent for the siloxane. Emulsion compositions are particularly useful.

20 Claims, No Drawings

ANTIMICROBIC, ANTISTATIC SILOXANE COMPOSITIONS AND METHOD FOR TREATING MATERIALS

BACKGROUND OF THE INVENTION

The present invention relates to a treatment agent for solid materials. More specifically, the present invention describes a treatment composition for solid materials which imparts a durable hydrophilicity, antistaticity and microbial resistance to solid materials.

Fungi such as many genera from the order Mucorales as well as Penicillium, Aspergillus and Rhizopus and Trichophyton and bacteria such as E. coli, Staphylococcus aureus, Corynebacterium, gram-negatives, Bacterium and Micrococcus, etc., proliferate by using as a food source the human perspiration or food or drink which may adhere to solid materials such as shoes, socks, underwear, casual wear, bedclothes such as sheets and covers and the interior materials of airplanes, ships and vehicles, etc. Offensive odors are then emitted.

To eliminate this problem, solid materials have heretofore been treated with organotin compounds, organomercury compounds, halogenated phenols, organocopper compounds, quaternary ammonium salt-containing cationic surfactants or quaternary ammonium salt-containing vinyl polymers, etc. However, these known treatment methods have not entered into widespread use because they exhibit poor durability with respect to washing and have unsatisfactory effects. Also, the treatment process entails problems such as environmental pollution and toxicity. A silane-type quaternary ammonium salt antimicrobial was then developed which has little toxicity for humans and it has received notice.

However, when such a silane-type quaternary ammonium salt is applied to a solid material, it has a very high water repellency and charging characteristic. As a result, it does not exhibit hydrophilicity in the form of water absorption, hygroscopicity or perspiration absorption on shoes, socks, underwear, casual wear, bedclothes and the interior materials of airplanes, ships and vehicles. In addition, solids thus treated become charged with static electricity and are thus easily soiled.

For this reason, in order to improve the hydrophilicity and antistaticity, solid materials such as fibers may be treated with the above-mentioned salt in combination with various hydrophilic surfactants or hydrophilic resins; however, the flexibility or lubricity of solid materials treated in this fashion will be degraded and these types of surfactants and resins, being easily washed off, are not durable.

BRIEF SUMMARY OF THE INVENTION

It is an object of the present invention to provide a composition for rendering a solid material durably antistatic, antimicrobic and hydrophilic. It is also an object of the present invention to provide a method for providing a durable antistatic, antimicrobic, hydrophilic silicone treatment for a solid material. It is a particular object of this invention to provide a method for conferring hydrophilicity and antistaticity properties to fibers and fiber-containing materials while also providing therefor a durable antimicrobial action.

These objects, and others which will become apparent upon consideration of the following disclosure and appended claims, are obtained by the method of this invention which, briefly stated, comprises treating a solid material with a composition which comprises, as its principal components, an organopolysiloxane compound which contains at least one siloxane unit bearing an alkoxysilylalkyl radical and at least one siloxane unit bearing a polyoxyalkylene radical, and an organosilane which possesses an antimicrobial activity and a reactivity with the organopolysiloxane compound.

In a preferred embodiment of this invention at least one of the alkoxysilylalkyl radicals is a siloxane chain-terminating radical.

DETAILED DESCRIPTION OF THE INVENTION

The present invention relates to a composition comprising (A) 100 parts by weight of a silane having the formula

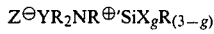

wherein $Z^\ominus$ denotes a halide ion, Y denotes a monovalent hydrocarbon radical containing from 10 to 20 carbon atoms, R denotes a monovalent hydrocarbon or halogenated hydrocarbon radical containing from 1 to 10 carbon atoms, R' denotes an alkylene radical having from 2 to 10 carbon atoms, X denotes an alkoxy radical or an alkoxyalkoxy radical containing from 1 to 4 carbon atoms and g has a value of 2 or 3, and (B) from 1 to 100 parts by weight of an organopolysiloxane compound which contains, in each molecule, at least one siloxane unit having the formula $X_aR_{(3-a)}SiR'''SiR_bO_{(3-b)/2}$ and at least one siloxane unit having the formula $R''(OC_3H_6)_c(OC_2H_4)_dOR'SiR_eO_{(3-e)/2}$ wherein R, R' and X are as noted above for component (A), R'' denotes a hydrogen atom or a monovalent organic radical having from 1 to 5 carbon atoms, R''' denotes an oxygen atom or an alkylene radical having from 2 to 4 carbon atoms, a=1, 2 or 3; b=0, 1 or 2; c=0 to 50; d=0 to 50; c+d=2 to 100; and e=1 or 2, any remaining siloxane units in the organopolysiloxane compound having the formula $R_fSiO_{(4-f)/2}$ wherein R has the meaning denoted above for components (A) and (B) and f=0, 1, 2 or 3.

By way of explanation, component (A) used in the present invention is the essential component for imparting microbial resistance to the solid material. It is a quaternary ammonium salt-containing silane with the general formula

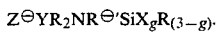

In the silane formula, Z represents a halogen atom and concrete examples thereof are the chlorine, bromine and iodine atoms. Y represents any monovalent hydrocarbon group having from 10 to 20 carbon atoms and concrete examples thereof are alkyl groups such as decyl, undecyl, dodecyl, tridecyl, octadecyl and eicosyl; alkenyl groups such as undecenyl, dodecenyl and octadecenyl and aryl groups. R' represents any alkylene group having from 2 to 10 carbon atoms and concrete examples thereof are ethylene, propylene, butylene, pentylene and octylene. Each R represents any monovalent hydrocarbon or halogenated hydrocarbon group having 1 to 10 carbon atoms and concrete examples thereof are alkyl groups such as methyl, ethyl and propyl; substituted alkyl groups such as 2-phenylethyl, 2-phenylpropyl and 3,3,3-trifluoropropyl and aryl and substituted aryl groups such as phenyl and tolyl. X represents any alkoxy group or alkoxyalkoxy group having 1 to 4 carbon atoms and concrete examples thereof are methoxy, ethoxy, propoxy, butoxy and methoxyethoxy and g is 2 or 3. Since this component is hydrolyzable, its partial hydrolysis condensates can also be employed.

This component has antimicrobial properties and can prevent the growth of fungi such as many genera from the order Mucorales as well as Penicillium, Aspergillus and Rhizopus and Trichophyton and bacteria such as *E. coli, Staphylococcus aureus,* Corynebacterium, gramnegatives, Bacterium and Micrococcus, etc.

Component (A) can be prepared by well-known methods from silanes having the formula $R_2NR'SiX_gR_{(3-g)}$ such as $(CH_3)_2NCH_2CH_2CH_2Si(OCH_3)_3$.

Component (B) used in the present invention is the essential component which reacts with component (A) to impart a durable hydrophilicity and antistaticity to solid materials. Each molecule of this component must contain at least 1 siloxane unit with the formula (1), $$X_aR_{(3-a)}SiR'''SiR_bO_{(3-b)/2} \quad (1)$$

at least 1 siloxane unit with the formula (2), $$R''(OC_3H_6)_c(OC_2H_4)_dOR'SiR_eO_{(3-e)/2} \quad (2)$$

and, optionally, other siloxane units having the formula (3), $$R_fSiO_{(4-f)/2}. \quad (3)$$

The siloxane (1) unit is the essential unit for increasing the binding and affinity to solid materials, as well as providing durability by the condensation reaction of molecular terminal alkoxy groups with an increase in molecular weight. The siloxane (2) unit is the essential unit for imparting antistaticity and hydrophilicity to the solid material.

In the above-mentioned formulas, X represents groups whose concrete examples are as cited for X in component (A). R''' represents an oxygen atom or any alkylene group having from 2 to 4 carbon atoms and concrete examples of the alkylene groups are ethylene, propylene and butylene. The R groups may or may not be identical and their concrete examples are as cited for R in component (A). R'' represents a hydrogen atom or monovalent organic group having from 1 to 5 carbon atoms and concrete examples of the monovalent organic groups are monovalent hydrocarbon groups such as methyl, ethyl, propyl, cyclohexyl, phenyl and β-phenylethyl, acyl groups and the carbamyl group.

In the preceding formulas a is an integer with value of 1 to 3, b is an integer with a value of 0 to 2, c and d are both integers with values of 0 to 50, (c+d) is an integer with a value of 2 to 100 and e is 1 or 2.

Concrete examples of siloxane units with formula (1) are $(CH_3O)(CH_3)_2SiO(CH_3)_2SiO_{\frac{1}{2}}$,
$(CH_3O)_3SiO(C_6H_5)(CH_3)SiO_{\frac{1}{2}}$,
$(CH_3O)_3Si(CH_2)_2(CH_3)SiO_{2/2}$,
$(CH_3O)_2(CH_3)Si(CH_2)_2(CH_3)_2SiO_{\frac{1}{2}}$,
$(C_2H_5O)_3Si(CH_2)_3SiO_{3/2}$,
$(C_2H_5O)_2(C_6H_5)Si(CH_2)_2(CH_3)_2SiO_{\frac{1}{2}}$,
$(C_3H_7O)_3Si(CH_2)_2(CF_3CH_2CH_2)SiO_{2/2}$, and
$(C_4H_9O)_3Si(CH_2)_3(C_2H_5)_2SiO_{\frac{1}{2}}$.

Concrete examples of siloxane units with formula (2) are $H(OC_3H_6)_{20}(OC_2H_4)_{20}O(CH_2)_3(CH_3)SiO_{2/2}$,
$H(OC_2H_4)_{10}O(CH_2)_5(C_2H_5)SiO_{2/2}$,
$H(OC_3H_6)_{15}O(CH_2)_3(CH_3)_2SiO_{\frac{1}{2}}$,
$CH_3(OC_3H_6)_{50}(OC_2H_4)_{30}O(CH_2)_3(CH_3)_2SiO_{\frac{1}{2}}$,
$C_2H_5(OC_2H_4)_{60}O(CH_2)_8SiO_{3/2}$,
$CH_3CO(OC_3H_6)_{25}(OC_2H_4)_{15}O(CH_2)_6(C_6H_5)SiO_{2/2}$, and
$C_2H_5CO(OC_3H_6)_{10}(OC_2H_4)_{40}O(CH_2)_2(CF_3CH_2CH_2)SiO_{2/2}$.

The instant organopolysiloxane must possess both types of units specified above. It can be constituted of only these 2 types of units or it may contain other organosiloxane units having the formula $R_fSiO_{(4-f)/2}$. The R groups bonded to silicon in these other organosiloxane units are monovalent hydrocarbon groups whose concrete examples are as cited above and f has a value of from 0 to 3.

Concrete examples of these other organosiloxane units are
$(CH_3)_2SiO_{2/2}$,
$(CH_3)_3SiO_{\frac{1}{2}}$,
$SiO_{4/2}$,
$CH_3SiO_{3/2}$,
$(CH_3)(CF_3CH_2CH_2)SiO_{2/2}$,
$(CH_3)(C_6H_5)SiO_{2/2}$,
$(C_6H_5)(CH_2)_2SiO_{3/2}$, etc.

The molecular structure of said organopolysiloxane is straight chain, branched chain, cyclic or network.

The degree of polymerization and molar proportions in the organopolysiloxane employed in the present invention are arbitrary. These are preferably determined from the standpoint of ease of treatment under the condition that the total number of siloxane units in each molecule is 5 to 500. In particular, when a lubricant property is desired, the total number of siloxane units should be at least 50.

In addition, since this component is hydrolyzable, its partial hydrolysis condensate can also be employed. This component is generally used at 1 to 100 weight parts and preferably 2 to 50 weight parts per 100 weight parts component (A).

In a preferred embodiment of the method of this invention the organopolysiloxane compound has a substantially linear structure with the formula $A(R_2SiO)_x(RQSiO)_y(RGSiO)_zSiR_2A$. In this formula Q denotes a radical having the formula $-R'''SiX_aR_{(3-a)}$, G denotes a radical formula $-R'O(C_2H_4O)_d(C_3H_6O)_cR''$, A denotes a siloxane chain-terminating radical selected from the group consisting of R, Q and G radicals, x has a value of from 1 to 500, y has a value of from 0 to 100 and z has a value of from 0 to 100, at least one Q radical and one G radical being present. The A radicals can be the same or different, as desired.

To increase the likelihood that substantially all of the molecules in the compound will durably adhere to a solid material when it is applied thereto it is preferred that at least one of said terminating radicals is a Q radical. To assure that substantially all of the molecules in the compound will durably adhere to a solid material when it is applied thereto it is preferred that both of said terminating radicals are Q radicals.

In the above formula the arrangement of the disubstituted siloxane units is not critical; however it is typically an approximately random arrangement. The arrangement of the siloxane units in the above formula has the conventional meaning and is not to be interpreted as requiring a block type arrangement of siloxane units. Furthermore, although the compounds of this invention are described as having a linear molecular structure, the presence of trace amounts of branching siloxane units having the formulae $SiO_{3/2}$ and $SiO_{4/2}$, frequently present in commercial organopolysiloxanes, are contemplated herein.

Concrete examples of the linear compounds used in this invention include, but are not limited to, those shown in the examples disclosed below and the following:

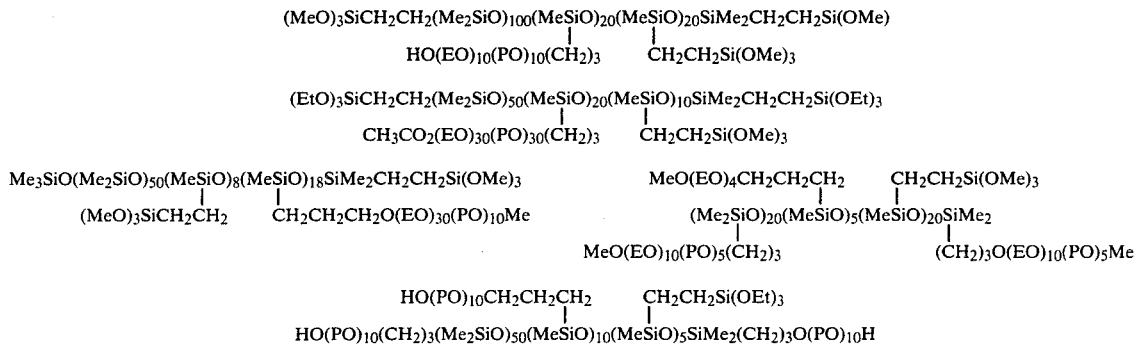

as well as compounds in which one silicon-bonded methyl group at the end of the preceding compounds is changed to phenyl or 3,3,3-trifluoropropyl, compounds in which all or part of the dimethylsiloxane units are changed to methylphenylsiloxane units or methyloctylsiloxane units and compounds in which some or all of the dimethylsiloxane units are changed to methyl(3,3,3-trifluoropropyl)siloxane units. Herein Me, Et, EO and PO denote $CH_3$, $CH_3CH_2$, $C_2H_4O$ and $C_3H_6O$, respectively.

The organopolysiloxane comprising this component is produced by, for example, the addition reaction of an organopolysiloxane with the formula

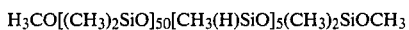

with an organosilane with the formula

and a polyether with the formula

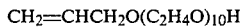

in the presence of a platinum-type catalyst.

The composition of the present invention is produced by simply mixing the prescribed quantity of component (A) with the prescribed quantity of component (B).

The composition of the present invention can be applied to a solid material as is or it may be coated on solid materials by dissolving it in an organic solvent such as toluene, xylene, benzene, η-hexane, heptane, acetone, methyl ethyl ketone, methyl isobutyl ketone, ethyl acetate, butyl acetate, mineral terpene, perchloroethylene or chlorothene to prepare a treatment solution which is subsequently coated on the solid material by spraying, roll coating, brush coating or immersion. Alternatively, the composition of the present invention can be emulsified and dispersed in water as is or it may be emulsified, for example, with an appropriate emulsifier such as a higher alcohol-polyoxyalkylene adduct, higher aliphatic acid-polyoxyalkylene adduct, higher aliphatic acid-sorbitan ester or alkylphenol-polyoxyalkylene adduct, etc., and then coated on the solid material by spraying, roll coating, brush coating or immersion.

The coated quantity of the instant composition is arbitrary and depends on the type of solid material to be treated; however, it is usually 0.1 to 5 weight percent based on the solid material.

The solid material which has been treated with the composition of the present invention can simply be allowed to stand at room temperature; however, after coating it is advantageously heated at 50° to 110° C. from the standpoints of process efficiency and increasing the durability. As a result, a durable hydrophilicity, antistaticity and microbial resistance are imparted to the solid material.

In addition, known additives such as curing catalysts, crosslinking agents, agents providing lubrication, thermal stabilizers and flame retardants, etc., can be added as necessary to the composition of the present invention.

The curing catalysts are known silanol condensation catalysts and consist of the organic acid salts of zinc, tin and zirconium, etc. Concrete examples are zinc stearate, zinc oleate, dibutyltin dioleate, dibutyltin dilaurate and zirconium stearate.

Concrete examples of the crosslinking agents are organohydrogenpolysiloxanes such as methylhydrogenpolysiloxane, alkoxysilanes such as amino group-containing alkoxysilanes and epoxy group-containing alkoxysilanes and silanol group-containing organopolysiloxanes.

Concrete examples of solid materials comprising the substrate for the application of the treatment composition of the present invention are various fibers and their fabrics; sheet materials such as paper, natural and synthetic leathers, cellophane and plastic films; foams such as synthetic resin foams; moldings such as synthetic resin moldings, natural and synthetic rubber moldings, metal moldings and glass moldings and powders such as inorganic powders and synthetic resin powders.

The materials comprising said fibers are exemplified by natural fibers such as hair, wool, silk, flax, cotton and asbestos; regenerated fibers such as rayon and acetate; synthetic fibers such as polyester, polyamide, vinylon, polyacrylonitrile, polyethylene, polypropylene and spandex; glass fibers; carbon fibers and silicon carbide fibers. The fibers may take the form, for example, of staple, filament, tow, yarn or thread. Concrete examples of the fabrics are knits, weaves, nonwovens, resin-finished fabrics and their sewn products.

EXAMPLES

The present invention will be explained using demonstrational examples. In the examples, part and % denote weight part and weight percent, respectively, and the viscosity is measured at 25° C.

The silanes and organopolysiloxanes employed in the examples have the following structural formulas A to H.

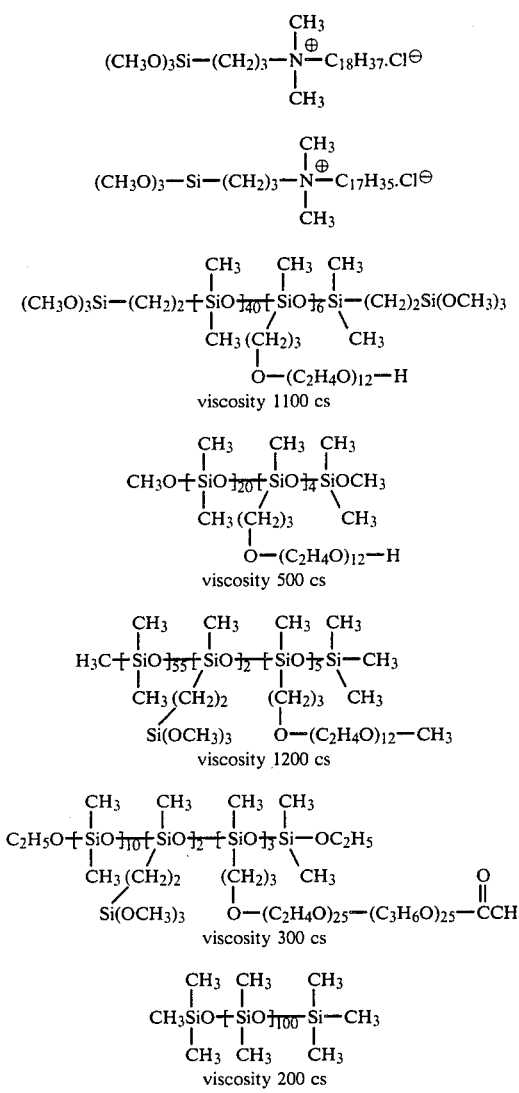

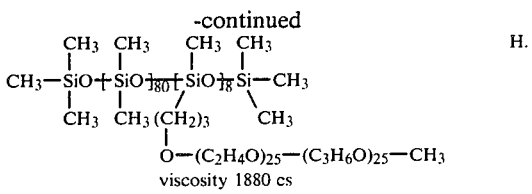

EXAMPLE 1

Three parts organopolysiloxane C are thoroughly mixed with 10 parts silane A and 987 parts methyl isobutyl ketone to prepare treatment liquid (a).

Treatment liquids (b), (c), (d) and (e) and treatment liquids (f) and (g) as comparison examples are similarly prepared using the compositions given in Table 1. In addition, treatment liquid (h) is prepared for comparison by dissolving 10 parts silane A in 990 parts methyl isobutyl ketone.

A 50% cotton/50% polyester knit (40×20 cm) is immersed in each of the treatment liquids for 30 seconds, treated on a mangle roll to a 100% expression, dried at room temperature for 5 hours and then heated in a hot air-circulation oven at 110° C. for 10 minutes.

The treated fabric is then cut into two pieces. One piece is washed in an automatic reversing washer once under the following conditions, then rinsed twice with water using the same conditions but omitting the detergent and then dried at room temperature: bath ratio, 1:50; temperature, 40° C.; detergent, Monogen (from Daiichi Kogyo Seiyaku Co., Ltd.); time, 10 minutes.

A water absorptivity test is conducted as follows. The treated fabrics, washed and unwashed, are laid out flat on filter paper. One drop of water is dripped onto each fabric using a fountain pen filler and the time period in seconds required for the diffusion and disappearance of the water drop is measured.

A charging test is conducted as follows. The treated fabric is allowed to stand at 20° C./65% RH for 1 week and is then rubbed with a cotton cloth (unbleached muslin No. 3) in a Kyoto University Chemical Research Laboratory rotary static tester at 800 rpm for 60 minutes. The triboelectrification voltage is then measured immediately.

In addition, the % residual silicone after washing is determined by measuring the counts for silicon before and after washing using an X-ray fluorescence analyzer from Rigaku Corp.

The results are reported in Table 1. The compositions of the present invention exhibited a good water absorptivity and antistaticity as well as an excellent durability with respect to washing.

TABLE 1

| Treatment Liquids | Composition *1 | Composition *2 | Water Absorptivity, (seconds) Pre-Wash | Water Absorptivity, (seconds) Post-Wash | Triboelectrification Voltage (V) Pre-Wash | Triboelectrification Voltage (V) Post-Wash | Residual Organopoly-siloxane After Washing, % |
|---|---|---|---|---|---|---|---|
| The Present Invention | | | | | | | |
| a | A | C | 0.5 | 35 | 1660 | 1790 | 77.8 |
| b | A | D | 0.5 | 39 | 1770 | 1850 | 76.7 |
| c | A | E | 0.3 | 34 | 1610 | 1690 | 74.5 |
| d | A | F | 0.5 | 38 | 1550 | 1620 | 74.0 |
| e | B | C | 0.4 | 37 | 1710 | 1780 | 75.3 |
| Comparison Examples | | | | | | | |
| f | A | G | ≧1200 | 995 | 2430 | 2290 | 35.5 |
| g | A | H | 0.4 | 135 | 1550 | 2290 | 30.3 |
| h | A | — | ≧1200 | 978 | 2330 | 2310 | 73.3 |
| Untreated Fabric | | | | | | | |

TABLE 1-continued

| Treatment Liquids | Composition *1 | *2 | Water Absorptivity, (seconds) Pre-Wash | Post-Wash | Triboelectrification Voltage (V) Pre-Wash | Post-Wash | Residual Organopoly-siloxane After Washing, % |
|---|---|---|---|---|---|---|---|
| None | None | None | 0 | 0 | 2250 | 2130 | 0 |

*1 = silane
*2 = siloxane

EXAMPLE 2

The left insole from a pair of commercial polyethylene foam insoles is treated on its top and bottom surfaces with treatment liquid (a) from Example 1 using a simple spray gun for 5 seconds on each side. The left insole from another pair is similarly treated with treatment liquid (h). These are then allowed to stand at room temperature overnight and then heated at 60° C. for 30 minutes.

The left insole treated with treatment liquid (a) and its untreated right insole are inserted into a pair of new canvas shoes which are subsequently worn by a person in a room at 28° C. for about 10 hours/day over 1 month. The socks worn are 100% nylon without an antimicrobial treatment and are changed daily for a fresh pair. One month after the start of the test, the insoles are removed and a charging test is conducted as in Example 1 and the odor is evaluated by organoleptic testing.

The used insoles are then washed and rinsed as described in Example 1 and subsequently again worn under the above conditions for 1 month. The resulting insoles are then removed and the charging is examined and the odor is evaluated by organoleptic testing.

The results are reported in Table 2. The present invention has an excellent antimicrobial characteristic and antistaticity and these properties are durable with respect to washing.

TABLE 2

| Treatment Liquid | After 1 Month Wear Unpleasant Odor | Triboelectrification Voltage (V) | After Washing and Then Another Month of Wear Unpleasant Odor | Triboelectrification Voltage (V) |
|---|---|---|---|---|
| Present Invention | | | | |
| a | Almost None | 2250 | Almost None | 2310 |
| Comparison Example | | | | |
| h | Almost None | 2480 | Almost None | 3520 |
| Untreated Fabric | | | | |
| — | Very Significant | 3880 | Very Significant | 3750 |

EXAMPLE 3

Treatment liquids (a') and (h') are prepared as described in Example 1 with the exception that water is used instead of the methyl isobutyl ketone dispersing solvent used for treatment liquids (a) and (h). Three pairs of commercial 100% cotton knit socks without an antimicrobial treatment are washed and post-treated under the washing conditions described in Example 1. Two of the pairs are treated by immersion in treatment liquids (a') or (h') heated to 60° C. for 60 minutes and then treated to give a 100% expression and then dried at room temperature overnight. The fit, lubricity and perspiration absorption are examined in the above-mentioned wear test.

The results are reported in Table 3. The socks treated with the treatment agent of the present invention exhibited a good fit, good lubricity and good perspiration absorption.

TABLE 3

| Treatment Liquid | Test Results for Wear |
|---|---|
| Present Invention | |
| a' | No starchy feel, excellent lubricity, excellent fit, excellent perspiration absorption |
| Comparison Example | |
| h' | Almost no starchy feel, inadequate lubricity, unsatisfactory fit, poor perspiration absorption |
| Untreated Fabric | |
| — | Significant starchy feel, poor fit, poor lubricity, poor recovery from elongation, good perspiration absorption |

EFFECT OF THE INVENTION

Since the treatment composition of the present invention for solid materials can impart a durable hydrophilicity, antistaticity and microbial resistance to solid materials as well as increasing the lubricity of the solid material, it is very suitably employed as an antimicrobial treatment agent for solid materials which require hydrophilicity and antistaticity.

That which is claimed is:

1. A composition comprising (A) 100 parts by weight of a silane having the formula

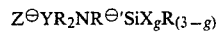

$$Z^{\ominus}YR_2NR^{\ominus\prime}SiX_gR_{(3-g)}$$

wherein $Z^{\ominus}$ denotes a halide ion, Y denotes a monovalent hydrocarbon radical containing from 10 to 20 carbon atoms, R denotes a monovalent hydrocarbon or halogenated hydrocarbon radical containing from 1 to 10 carbon atoms, R' denotes an alkylene radical having from 2 to 10 carbon atoms, X denotes an alkoxy radical or an alkoxyalkoxy radical containing from 1 to 4 carbon atoms and g has a value of 2 or 3, and (B) from 1 to 100 parts by weight of an organopolysiloxane compound which contains, in each molecule, at least one siloxane unit having the formula $$X_aR_{(3-a)}SiR'''SiR_bO_{(3-b)/2}$$

and at least one siloxane unit having the formula $$R''(OC_3H_6)_c(OC_2H_4)_dOR'SiR_eO_{(3-e)/2}$$

wherein R, R' and X are as noted above for component (A), R" denotes a hydrogen atom or a monovalent organic radical having from 1 to 5 carbon atoms, R''' denotes an oxygen atom or an alkylene radical having from 2 to 4 carbon atoms, $a=1$, 2 or 3; $b=0$, 1 or 2; $c=0$ to 50; $d=0$ to 50; $c+d=2$ to 100; and $e=1$ or 2, any remaining siloxane units in the organopolysiloxane compound having the formula $R_fSiO_{(4-f)/2}$ wherein R has the meaning denoted above for components (A) and (B) and $f=0$, 1, 2 or 3.

2. A composition according to claim 1 wherein the organopolysiloxane compound has the formula $$A(R_2SiO)_x(RQSiO)_y(RGSiO)_zSiR_2A$$

wherein
Q denotes a radical having the formula $-R'''SiX_aR_{(3-a)}$,
G denotes a radical having the formula $-R'O(C_2H_4O)_d(C_3H_6O)_cR''$,
A denotes a radical selected from the group consisting of R, Q and G radicals,
x has a value of from 1 to 500,
y has a value of from 0 to 100 and
z has a value of from 0 to 100,
there being at least one Q radical and one G radical in the organopolysiloxane.

3. A composition according to claim 2 wherein each R radical is a methyl radical.

4. A composition according to claim 3 wherein each X radical is a methoxy radical.

5. A composition according to claim 4 wherein one A radical is a methyl radical.

6. A composition according to claim 4 wherein one A radical is a Q radical.

7. A composition according to claim 4 wherein one A radical is a G radical.

8. A composition according to claim 4 wherein both A radicals are Q radicals.

9. A composition according to claim 4 wherein both A radicals are G radicals.

10. A composition according to claim 4 wherein both A radicals are methyl radicals.

11. A composition according to claim 1 wherein the organopolysiloxane compound has the formula $Me_3SiO(Me_2SiO)_x(MeQSiO)_y(MeGSiO)_zSiMe_2Q$ wherein x, y and z are positive integers and Me denotes methyl.

12. A composition according to claim 11 wherein Q denotes the $-CH_2CH_2Si(OMe)_3$ radical.

13. A composition according to claim 1 wherein the composition further comprises a curing amount of a curing agent comprising a curing catalyst and/or a crosslinking compound for silanol groups.

14. A composition according to claim 13 wherein the composition is an aqueous emulsion.

15. A composition according to claim 2 wherein the composition further comprises a curing amount of a curing agent comprising a curing catalyst and/or a crosslinking compound for silanol groups.

16. A composition according to claim 15 wherein the composition is an aqueous emulsion.

17. A composition according to claim 11 wherein the composition further comprises a curing amount of a curing agent comprising a curing catalyst and/or a crosslinking compound for silanol groups.

18. A composition according to claim 17 wherein the composition is an aqueous emulsion.

19. A method for treating a solid material, said method comprising applying to the solid material an amount of a composition comprising the composition of claim 1, said amount being sufficient to provide antistatic, hydrophilic, antimicrobic properties to the solid material.

20. A method according to claim 19 wherein the solid material comprises a fiber.

* * * * *